(12) United States Patent
McGuinness et al.

(10) Patent No.: US 9,005,983 B2
(45) Date of Patent: Apr. 14, 2015

(54) ELECTRO-CHEMICAL SENSOR

(75) Inventors: Kay McGuinness, Milton (GB); Nathan Lawrence, Wyton (GB); Andrew Meredith, Cambridge (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 465 days.

(21) Appl. No.: 13/062,788

(22) PCT Filed: Aug. 26, 2009

(86) PCT No.: PCT/IB2009/006637
§ 371 (c)(1),
(2), (4) Date: Nov. 26, 2011

(87) PCT Pub. No.: WO2010/026456
PCT Pub. Date: Mar. 11, 2010

(65) Prior Publication Data
US 2012/0064632 A1    Mar. 15, 2012

(30) Foreign Application Priority Data
Sep. 8, 2008  (GB) .................................. 0816317.2

(51) Int. Cl.
*G01N 33/20* (2006.01)
*G01N 30/00* (2006.01)
*G01N 33/24* (2006.01)

(52) U.S. Cl.
CPC ...................................... *G01N 33/24* (2013.01)

(58) Field of Classification Search
CPC ....... G01N 33/84; G01N 31/22; G01N 31/16; G01N 33/1853; G01N 33/20; G01N 33/1813; G01N 21/3103; G01N 21/78; G01N 21/29; G01N 27/00; C07D 498/08; C02F 1/72; A61K 31/295; A61K 31/7016; A61K 33/26

USPC ......... 436/79, 73, 83, 84, 182, 80, 81; 422/69
See application file for complete search history.

(56) References Cited

U.S. PATENT DOCUMENTS

| 5,296,123 A | 3/1994 | Reddy et al. |
| 5,437,772 A | 8/1995 | De Castro et al. |

(Continued)

FOREIGN PATENT DOCUMENTS

| DE | 19939901 A | 12/2000 |
| DE | 29923868 U | 8/2001 |

(Continued)

OTHER PUBLICATIONS

Yu E Alexeev, I S Vasilchenko, B I Kharisov, L M Blanco, A D Garnovskii and Yu A Zhdanov; "Review: Synthetically modified carbohydrates as ligands"; Journal of Coordination Chemistry, 57 (2004) pp. 1447-1517.

(Continued)

*Primary Examiner* — Krishnan S Menon
*Assistant Examiner* — Dwan A Gerido (57) ABSTRACT

The present invention provides an electrochemical sensor having a solid electrically conductive substrate and a compound immobilized thereon which has binding affinity for an analyte species to be detected and also displays electrochemical behavior which is modified upon binding of that analyte species, so that binding of an analyte species can be detected by measuring electrochemical properties, such as by voltammetry. Desirably the immobilized compound contains both a first moiety with binding affinity for the analyte and a separate second moiety which is a redox system whose electrochemical oxidation/reduction properties become modified when the first moiety binds the analyte. The analyte binding moiety may be a diol or polyol and preferably is a sugar. The electrochemical sensor finds use in methods of analyzing reservoir and process fluids, particularly at a subterranean location. The electrochemical sensor may be a component of a downhole tool, adapted for deployment downhole.

21 Claims, 1 Drawing Sheet

(56) References Cited

U.S. PATENT DOCUMENTS

| | | | |
|---|---|---|---|
| 5,534,132 | A | 7/1996 | Vreeke et al. |
| 5,676,820 | A | 10/1997 | Wang et al. |
| 5,942,388 | A * | 8/1999 | Willner et al. ............... 435/6.11 |
| 6,432,723 | B1 | 8/2002 | Plaxco et al. |
| 6,458,600 | B1 | 10/2002 | Mirsky et al. |
| 6,989,102 | B1 | 1/2006 | Park et al. |
| 2001/0042693 | A1 | 11/2001 | Onitskansky et al. |
| 2003/0008779 | A1 | 1/2003 | Chen et al. |
| 2003/0083204 | A1 | 5/2003 | Chatterji et al. |
| 2005/0003398 | A1* | 1/2005 | Tao et al. .................... 435/6 |
| 2005/0178548 | A1 | 8/2005 | Robinson et al. |
| 2007/0205157 | A1 | 9/2007 | Jones et al. |
| 2008/0161209 | A1 | 7/2008 | Wood |
| 2009/0272693 | A1 | 11/2009 | Mabille et al. |
| 2011/0048969 | A1* | 3/2011 | Lawrence et al. ............. 205/775 |

FOREIGN PATENT DOCUMENTS

| | | | |
|---|---|---|---|
| GB | 2391314 | A | 2/2004 |
| GB | 2395555 | A | 5/2004 |
| GB | 2404252 | A | 1/2005 |
| GB | 2409902 | A | 7/2005 |
| GB | 2420849 | A | 6/2006 |
| GB | 2430749 | A | 4/2007 |
| JP | 2001340873 | A | 12/2001 |
| JP | 2007505323 | A | 3/2007 |
| KR | 20040000645 | A | 1/2004 |
| WO | WO03021247 | A1 | 3/2003 |
| WO | WO2005026694 | A2 | 3/2005 |
| WO | WO2005066618 | A1 | 7/2005 |
| WO | WO2006114501 | A1 | 11/2006 |
| WO | WO2007106936 | A1 | 9/2007 |

OTHER PUBLICATIONS

Philippe Allongue, Michel Delamar, Bernard Desbat, Olivier Fagebaume, Rachid Hitmi, Jean Pinson and Jean-Michel Save'ant; Covalent Modification of Carbon Surfaces by Aryl Radicals Generated from the Electrochemical Reduction of Diazonium Salts; J. Am. Chem. Soc. 1997, 119, 201-207.

Claude P. Andrieux, Felipe Gonzalez, and Jean-Michel Save'ant; Derivatization of Carbon Surfaces by Anodic Oxidation of Arylacetates: Electrochemical Manipulation of the Grafted Films; J. Am. Chem. Soc. 1997, 119, 4292-4300.

Antoniadou S, Jannakoudakis A D, Jannakoudakis P D and Theodoridou E; Anion exchange activity of electrochemically bonded ethylene diamine on carbon fibres; Journal of Applied Electrochemistry vol. 22 pp. 1060-1064 (1992).

Barbier B, Pinson J, Desarmot G, & Sanchez M; Electrochemical bonding of amines to carbon fiber surfaces toward improved carbon-epoxy composites; J. Electrochem. Soc., vol. 137, No. 6, Jun. 1990.

P D Beer; Transition-Metal Receptor Systems for the Selective Recognition and Sensing of Anionic Guest Species; Acc Chem Res 31 (1998) 71-80.

B Bildstein, M Malaun, H Kopacka, K.-H Ongania and K Wurst; Imidazoline-2-ylidene metal complexes with pendant ferrocenyl substituents; J. Organometallic Chem., 552 (1998) 45.

J. R. Deans, B. G.Dixon; Uptake of Pb2+ and Cu2+ by novel biopolymers; Water Res. 26, 469, (1992).

R. P. Deo, J. Wang; Electrochemical detection of carbohydrates at carbon-nanotube modified glassy-carbon electrodes; Electrochem. Commun., 6 (2004) 284.

H Eckert and C Seidel; The Ferrocenylmethyl(Fem) Group as a Highly Lipophilic and Chromophoric Group for the Masking of Peptide Bonds; Angew. Chem. Int. Ed. Engl., 25 (1986) 159.

H. Eckert, B. Forster, C. Seidel: Total masking -Gly bonds by highly lipophilic and chromophoric ferrocenylmethyl [Fem] residue in peptide synthesis of hexaglycine and leu-enkephalin; Zeitschrift für Naturforschung B 46 (1991) 339; in German with English abstract.

H. Ei-Saied, A. H. Basta; "Grafting of some carbohydrates with multigroup chelating monomer"; J. Carb. Chem., 18 (1999) 585.

M. Gerecke, R. Borer, A. Brossi, "274. Selective Ether Cleavage in the Aporphine Series. Conversion of (S)-Bulbocapnine into (S)-Corytuberine and (S)-Corydine Methyl Ether"; Helv. Chim. Acta, 59 (1976) 2251.

Guo B., Anzai J. and Osa T.; Modification of a glassy carbon electrode with diols for the suppression of electrode fouling in biological fluids; Chem.Pharm.Bull 44 860-862 (1996).

Hayes M A & Kuhr W G Preservation of NADH Voltammetry for Enzyme-Modified Electrodes Based on Dehydrogenase; Anal. Chem. 1999, 71, 1720-1727.

S. Hughes, D.C. Johnson; Amperometric detection of simple carbohydrates at platinum electrodes in alkaline solutions by application of a triple pulse potential waveform; Anal. Chim. Acta, 132 (1981) 11.

Ioffe, Tartakovskii, Novikov, "Selective reduction of aliphatic nitro-compounds with other functional groups"; Russ. Chem Rev., 35 (1966) 19.

Jang, L. K., Lopez, S. L., Eastman, S. L., Pryfolge, P.; Recovery of Copper and Cobalt by Biopolymer Gels; Biotechnol. Bioeng., 37, 266, (1991).

C Jeon, W H Höll; Chemical modification of chitosan and equilibrium study for mercury ion removal; Water Research 37 (2003) 4770-4780.

B A Keay and R Rodrigo; Intramolecular Diels-Alder reaction of an isobenzofuran: a convergent synthesis of resistomycin; J. Am. Chem. Soc., 104, (1982) 4725-7.

"A S Kende and D P Curran; Regiochemical Control in Dihydrophenanthrene Synthesis. A Photochemical Total Synthesis of Juncusol; J. Am. Chem. Soc., 101 (1979) 1857;".

K. Kondo, S. -I. Nakagawa, M. Matsumoto, T. Yamashita, I. Furukawa; Selective adsorption of metal ions on novel chitosan-supported sulfonic acid resin; J. Chem. Eng. Jap., 30 (1997) 846.

E. P. Kuncoro, J. Roussy, E. Guibal; Mercury Recovery by Polymer-Enhanced Ultrafiltration: Comparison of Chitosan and Poly(Ethylenimine) Used as Macroligand; Separation Science and Technology, 40 (2005) 659.

S. Loonker, S. K. Gaur, K. Daga, V. Gupta, P. Mishra; Synthesis and application of Ion selective chelating resin derived from guar; Asian J. Chem., 14 (2002) 395.

J. Marioli, T. Kuwana; Electrochemical Detection of Carbohydrates•at Nickel—Copper and Nickel—Chromium—Iron Alloy Electrodes; Electroanalysis, 5 (1993) 11.

J C Medina, T T Goodnow, M T Rojas, J L Atwood, B C Lynn, A E Kaifer and G W Gokel; Ferrocenyl iron as a donor group for complexed silver in ferrocenyldimethyl[2.2]cryptand: a redox-switched receptor effective in water; J. Am. Chem. Soc., 114 (1992) 10583-10595.

A. Mikan, M. Bartusek; The reactions of oligoalcohols with arsenic, arsenous, boric and germanic acids; Collect. Czech. Chem. Commun., 45 (1980) 2645.

M Node, K Nishide, M Sai, K Ichikawa, K Fuji, E Fujita; Aluminium halide-thiol system: a useful reagent for demethylation of aliphatic and aromatic methyl ethers and demethylenation of methylene dioxy compounds; Chemistry Letters, 1979 pp. 97-98.

M Pandurangappa, N. S. Lawrence, R. G. Compton; Homogeneous chemical derivatisation of carbon particles: a novel method for funtionalising carbon surfaces. Analyst, vol. 127, p. 1568 (2002).

H Plenio and C Aberle; Synthesis of a ferrocene bridged cyclam: a new redox-active macrocycle and the structure of a nickel(ii) complex with strongly coupled metal centers; Chemical Communications 24 (1998) 2697-2698.

H Plenio and C Aberle; Oxaferrocene Cryptands as Efficient Molecular Switches for Alkali and Alkaline Earth Metal Ions; Organometallics 16 (1997) 5950-5957.

H Plenio and D Burth; Aminoferrocenes and Aminocobaltocenes as Redox-Active Chelating Ligands: Syntheses, Structures, and Coordination Chemistry; Organometallics 15 (1996) 4054-4062.

Z. Reddad, C. Gerente, Y. Andres, P. Le Cloirec; Lead removal by a natural polysaccharide in membrane reactors; Water Science and Technology, 49 (2004) 163.

J. A. Rendleman; Complexes of Alkali metals and Alkaline-Earth metals with carbohydrates; Adv. Carbohydr. Chem., 21 (1966) 209.

(56) References Cited

OTHER PUBLICATIONS

L.M. Santos, R.P. Baldwin; Liquid chromatography/electrochemical detection of carbohydrates at a cobalt phthalocyanine containing chemically modified electrode; Anal. Chem., 59 (1987) 1766.

J. Shao, Y. Yang, C. Shi; Preparation and Adsorption Properties for Metal Ions of Chitin Modified by L-Cysteine; Journal of Applied Polymer Science, 88 (2003) 2575.

H-A. Tajmir-Riahi; Carbohydrate adducts with zinc-group-metal ions. Interactions of β-d-fructose with Zn(II), Cd(II), and Hg(II) cations, and the effects of metal-ion coordination on the sugar isomer binding; Carbohydr. Res., 172 (1988) pp. 1-10.

H-A. Tajmir-Riahi; Sugar interaction with metal ions: synthesis, spectroscopic, and structural analysis of Zn(II), Cd(II), and Hg(II) complexes, containing d-glucuronate anion P; J. Inorg. Biochem., 26 (1986) 23.

S. Tan, Y. Wang, C. Peng, Y. Tang; Synthesis and Adsorption Properties for Metal Ions of Crosslinked Chitosan Acetate Crown Ethers; Journal of Applied Polymer Science, 71 (1999) 2069.

J. Gonzalez Velasco, S. Ayllon, J. Sancho; Study of complexes between D(+) saccharic acid and Al(III), Ga(III), Cr(III) and Mo(VI) ions, by electrophoretic methods; J. Inorg. Nucl. Chem., 41 (1979) 1075.

A. Vesala, H. Linnberg, R. Kippi, J. Arpalahti; Stoichiometry of the complexes of methyl glycofuranosides with metal ions in aqueous solution; Carbohydr. Res., 102 (1982) 312.

J. Wang, Z. Taha; Catalytic oxidation and flow detection of carbohydrates at ruthenium dioxide modified electrodes; Anal. Chem. 62 (1990) 1413.

M. Weltrowski, B. Mattel, M. Morcellet; Chitosan N-Benzyl Sulfonate Derivatives as Sorbents for Removal of Metal Ions in an Acidic Medium; J. App. Pol. Sci., 59 (1996) 647.

L Xiao, R Kitzler, and W Weissensteiner; O-Methylephedrine: A Versatile and Highly Efficient ortho-Directing Group. Synthesis of Enantiopure 1,2-Disubstituted Ferrocene Derivatives J. Org. Chem., 66 (2001) 8912-8919.

F W Ziegler, K W Fowler and S Kanfer; The chemospecific, homogeneous, ambient temperature Ullmann coupling of o-haloarylimines; J. Am. Chem. Soc., 98 (1976) 8282.

A Zirino, S H. Lieberman, and C Clavell; Measurement of copper and zinc in San Diego Bay by automated anodic stripping voltammetry; Environ. Sci. Technol. 12 (1978) 73.

C. Jeon, H. P. Kwang; Adsorption and desorption characteristics of mercury(II) ions using aminated chitosan; Water Research, 39 (2005) 3938.

GB Combined Search and Examination Report Dec. 12, 2008.

PCT Search Report and Written Opinion Mar. 24, 2010.

* cited by examiner

ELECTRO-CHEMICAL SENSOR

This invention relates to electrochemical sensors for determining constituents of fluids. Fields in which the invention may be utilised include, although are not restricted to, the analysis of water at the Earth's surface and also the analysis of a subterranean fluids which may be in an aquifer or downhole in a hydrocarbon reservoir.

BACKGROUND OF THE INVENTION

There are numerous circumstances in which it is desirable to detect, measure or monitor a constituent of a fluid. These include the detection and/or determination of trace metal ions and other species which may occur in aqueous fluids which may for example be a water supply or an effluent.

A particularly challenging context is the analysis of downhole fluids, which can be an important aspect of determining the quality and economic value of a hydrocarbon formation. Knowledge of downhole formation (produced) water chemistry can be applied to save costs and increase production at all stages of oil and gas exploration and production. Measurements obtained downhole can be important for a number of key processes of hydrocarbon production, including:

- Prediction and assessment of mineral scale and corrosion;
- Strategy for oil/water separation and water re-injection;
- Understanding of reservoir compartmentalization/flow units;
- Characterization of water break-through;
- Derivation of the water cut $R_w$; and
- Evaluation of downhole $H_2S$ partition in the oil and or water (if used for $H_2S$ measurements).

Analysis downhole can be valuable because some species contained within a reservoir fluid may be responsible for disadvantageous properties of the fluid, including potential to cause damage to well apparatus that comes into contact with that fluid. Some species within a reservoir fluid, for example heavy metal ions, may potentially have harmful environmental impact if brought to the surface. Analysis of fluids is also relevant to determining the chemistry of a waterbody which may be surface water, groundwater or water in an aquifer. Here too there can be a requirement to detect or determine metal ions.

There have been proposals for electrochemical analytical sensors to be used downhole. Examples include sensors focused on the detection of $H_2S$, pH or the group II scaling ions: Ba, Ca and Sr. See, for example, GB2391314; GB2409902; GB2430749; GB2395555 and GB2404252. Some electrochemical sensors have been directed to the monitoring of trace metals in natural waters. Zirino et al have developed an automated flow system for the continuous measurement of trace metals in sea-water by a method based on anodic stripping voltammetry. U.S. Pat. No. 5,296,123, U.S. Pat. No. 5,437,772, U.S. Pat. No. 5,676,820 and US2001/0042693 disclose sensors for quantification of trace metals (Cd, Cu, Fe, Pb, Ni and Zn) in water and effluent.

In GB2404252 above the sensor includes a ligand which is able to bind to scaling ions and has an electronic configuration which is altered on binding of a scaling ion. The electroactivity of the ligand is then monitored to detect whether a change in electroactivity, which denotes binding by a scaling ion, has taken place. The ligand may be in solution, confined by a membrane, or may be immobilised on conducting particles attached to an electrode.

It has been known for a number of years that the binding of an ion to a ligand can be observed as a change in electrochemical properties and moreover that the change can be observed as a change in electrochemical properties of a redox system adjacent to the bound ligand. This has been demonstrated with ligands bound to metallocenes as redox system. See papers by Plenio et al, by Beer and by Medina et al in the list of references.

The ligands which have been employed have often been macrocyclic compounds such as crown ethers. Preparation of the ligand has sometimes entailed the elaboration of a multistep synthesis. The electrochemistry has generally been carried out with the metallocene-ligand compound, in solution and its complex with a metal ion likewise in solution.

SUMMARY OF THE INVENTION

Broadly, the present invention provides an electrochemical sensor in which a chemical entity to bind a species to be detected (referred to as an analyte) is immobilised on a support and binding is observed through a consequent change in electrochemical properties.

According to a first aspect of this invention an electrochemical sensor comprises an electrically conductive solid substrate, immobilised on which is at least one compound which
  (i) is an organic diol or polyol with binding affinity for an analyte species and
  (ii) displays electrochemical behaviour which is modified upon binding of the analyte species.

Preferably this compound comprises a sugar which provides the binding affinity for the analyte species.

The sensor may be used to detect qualitatively whether the analyte species is present in a fluid or, more preferably, can be used to determine quantitatively the concentration of the analyte species.

Sugars are of course polyhydroxy compounds. The term sugar is used here to include unmodified carbohydrates and also compounds with characteristic saccharide structure but with modifications to the attached functional groups. Thus a sugar may be defined as comprising one or more saccharide units, each of which is a pentose or hexose, or possibly a tetrose or heptose, optionally modified by formal variation or derivatisation of one, two or possibly three hydroxy groups.

Examples of formal variation include replacement of hydroxy by amino to give an amino sugar, and replacement of hydroxy with hydrogen to give a deoxy sugar. Examples of derivitisation include esterification of a hydroxy group and conversion of a hydroxy group to a methoxy group. Such modification is called "formal" because it denotes the product which would be obtained, but without limitation as to whether or not the product is actually obtained by reaction of an existing hydroxyl group.

The present inventors have recognised that sugar groups may be used to bind to analyte species and are advantageous, for reasons which include availability and cost. Furthermore, because a large number of sugar groups are known, it is possible to choose sugars to give selectivity for one analyte species over other species in the test fluid. This advantageous possibility is further enhanced when it is considered that sugar groups may be derivatised to further improve selectivity and binding characteristics.

It is possible, and included within the scope of this invention, that the sugar itself will provide both binding affinity for an analyte species and redox chemistry which can be observed by electrochemistry. However, the redox reactions of many sugars take place under strongly alkaline conditions which are unlikely to be provided by a fluid which it is desired to test.

Consequently, in preferred forms of the invention, this binding compound which has affinity for an analyte species and displays electrochemical behaviour which is modified upon binding of the analyte species, contains both a sugar with binding affinity for the analyte species and also a non-sugar redox system whose electrochemical oxidation/reduction properties become modified when the sugar binds the analyte species.

In a second aspect of this invention an electrochemical sensor comprises an electrically conductive solid substrate, immobilised on which is at least one organic compound which has binding affinity for an analyte species and displays electrochemical behaviour which is modified upon binding of the analyte species, characterized in that the compound contains both a first moiety with binding affinity for the analyte species and a second moiety which is a redox system whose electrochemical oxidation/reduction properties become modified when the first moiety binds the analyte species.

The moiety with binding affinity for the analyte species may be a diol or polyol and more preferably may be a sugar.

In use, the electrically conductive substrate will generally constitute the working electrode of an electrochemical cell. An electrochemical sensor of this invention will generally also contain a reference electrode which may be metallic, for example a noble metal.

It will be appreciated from the discussion above that preferred forms of this invention will have an electrically conductive support, a moiety with binding affinity for the analyte species and a redox system which is distinct from the binding moiety. The redox system may be covalently joined to the binding moiety, either directly through a single covalent bond or indirectly through a linker group which is covalently connected to both the binding moiety and the redox system. The binding moiety or the redox system may be attached chemically to the support. Again this may be attachment directly or through a linker group. One arrangement which is envisaged is that the binding moiety is attached to the redox system and the redox system is attached to the support so that the redox system itself provides a linking group between the binding moiety and the support.

In a further aspect this invention provides a method of detecting or determining an analyte species in a fluid, comprising contacting the fluid with an electrochemical sensor according to one of the above-mentioned aspects of this invention and measuring the electrochemical behaviour of the said compound. Observation of electrochemical properties may be carried out potentiometrically, voltametrically, amperometrically, or coulometrically.

The invention also provides a tool, which may be a surface tool or a downhole tool such as a wireline tool or a slickline tool, incorporating an electrochemical sensor according to one of the above-mentioned aspects of this invention. The tool may be constructed to take a sample of fluid and bring this into contact with the sensor, or alternatively to expose the sensor to the main bulk of the fluid.

Downhole measurement tools for oilfield applications are known as such. An electrochemical technique using a sensor in accordance with the present invention can be applied for example as part of a production logging tool or an open hole formation tester tool for use in a well drilled for oil or gas. In such a case, the invention may be used in providing a downhole real-time assessment of water which in turn can be used for predicting mineral scale and for corrosion assessment. Such tools may be devices lowered into a well by means of a cable, such as wireline or slickline, or may be tools carried into a well by coiled tubing, or even tools which are positioned downhole for a longer period.

Downhole measurement tools are also used in wells drilled to monitor groundwater or to access subterranean aquifers. A sensor in accordance with the invention can be utilised in such tools.

If the sensor is incorporated into a surface tool, this may be a component part of any piece of equipment that comes into contact with the fluid of interest. It may for instance be fitted to a pipeline at the surface to monitor fluid flowing in that pipeline.

These and other features of the invention, preferred embodiments and variants thereof, possible applications and advantages will become appreciated and understood by those skilled in the art from the following detailed description and drawings.

DETAILED DESCRIPTION

Figure 1:
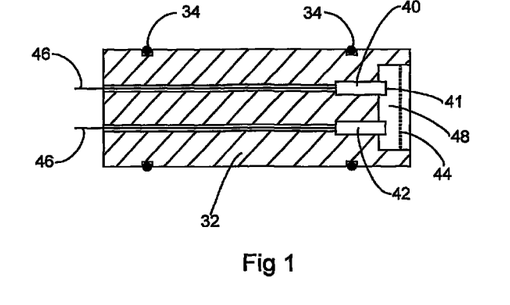
FIG. 1 is a diagrammatic cross section of an electrochemical sensor unit embodying the invention.

FIG. 1 illustrates in cross section a sensor unit embodying the invention. It has a main body 32 which is cylindrical and made of an insulating material. This body is intended to be accommodated inside a cylindrical cavity in a wellbore tool or other structure and is encircled by two sealing rings 34 to provide a seal between the body 32 and the cavity accommodating it. The body 32 supports a working electrode 40 and a counter electrode 42. Electrical connections to the electrodes are indicated at 46. The electrode 40 provides an electrically conductive substrate, immobilised on surface 41 of which is an organic chemical compound with binding affinity for an analtye species and which also provides a redox system whose electrochemistry is altered when the compound binds an analyte species, as required by this invention. This surface 41 and an end portion of the counter electrode 42 are exposed within a cavity 48 at the end 49 of the body 32. A porous shield 44 allows fluid to enter the cavity 48 but protects the electrodes from impact damage.

Figure 2:
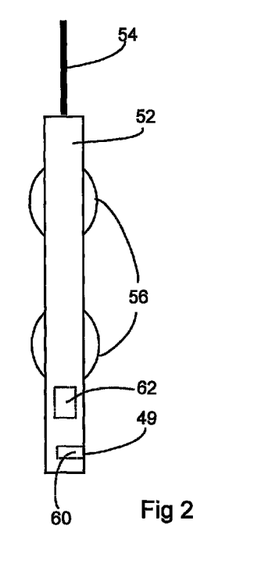
FIG. 2 is a diagrammatic illustration of a wireline tool incorporating the sensor unit of FIG. 1.

FIG. 2 diagrammatically illustrates a wireline tool with a generally cylindrical body 52 suspended at the lower end of a wireline 54. The body 52 is provided with centralisers 56 for positioning it within a wellbore. The body 52 may house a variety of devices for making measurements on the wellbore, the surrounding geological formation and on fluid within the wellbore. Amongst these is a sensor unit 60 such as that of FIG. 1. This is fitted into a cavity within the body 52 so that the end 49 of the sensor unit 60 is exposed to the fluid within the wellbore. The tool body 52 also encloses a unit 62 for supplying voltage to the electrodes of the sensor unit 60, measuring the current which flows and communicating the results to the surface via the wireline cable.

A wireline tool such as that diagrammatically illustrated by FIG. 2 could be configured and used to determine the producing zones of an oil production well. For vertical and near vertical wells, the tool is suspended from the wireline cable which is used to lower and raise the tool within the well. For highly deviated wells, the tool is pushed or pulled using coiled tubing from the surface, or a tractor powered and controlled by cable from the surface. In analogous manner a wireline tool could be configured and used to investigate an underground body of water contacted by a well drilled into an aquifer.

A sensor in accordance with this invention could also be incorporated into a wide variety of other tools and equipment. Possibilities include use in tools which are located permanently downhole, use in tools which are conveyed downhole at the head of coiled tubing, use in underground, undersea or surface pipeline equipment to monitor liquid flowing in the pipeline, and use in various kinds of process plant at the Earth's surface.

Figure 3:
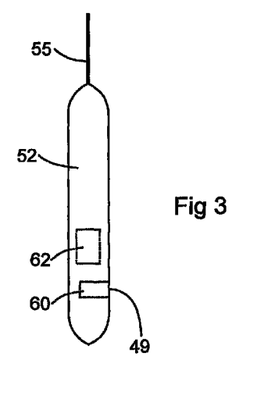
FIG. 3 is a diagrammatic illustration of a cable-suspended tool for testing water.

A sensor in accordance with this invention may well be used outside the oil and gas industry. Use in water treatment can be envisaged, as can use in a wide variety of other areas of science and industry. FIG. 3 illustrates a tool for investigating subterranean water. This tool also has a cylindrical body 52 which is suspended from a cable 55. A sensor unit 60 is accommodated within the body so that its end 49 is exposed to the subterranean water. The tool also encloses a unit 62 for supplying voltage to the electrodes of the sensor unit 60, measuring the current which flows and transmitting the results to the surface.

Immobilised Binding Compound

The invention requires an organic compound which provides both binding affinity for an analyte species and an electrochemistry which shows a detectable change when an analyte species is bound. This compound, or a binding moiety within such a compound, is preferably a sugar, or a variant or derivative of a sugar containing one or more saccharide units.

The sugar may be a monosaccharide, disaccharide, oligosaccharide (typically 3 to 10 saccharide units) or polysaccharide (typically 11 or more saccharide units). Where there are two or more saccharide units in the sugar, a unit may be the same or different to its neighbour or neighbours.

Each saccharide unit may be independently derived from a four carbon carbohydrate (a tetrose) a five carbon carbohydrate (a pentose) a six carbon carbohydrate (a hexose) or possibly even a seven carbon carbohydrate (a heptose), where the number of carbon atoms is the number of atoms in the main chain.

Each saccharide unit may be independently in an aldose or ketose form, independently in a D- or L-form and independently in the α- or β-form. Where there are two or more saccharide units in a sugar, the units may be α- or β-linked or a mixture of both.

Each saccharide unit may be independently selected from furanose and pyranose forms, where appropriate.

A saccharide unit derived from a four carbon carbohydrate may be independently selected from erythrose, threose, the branched carbohydrate apiose and variants and derivatives thereof. The D-forms are most preferred.

A saccharide unit derived from a five carbon carbohydrate may be independently selected from ribose, arabinose, xylose, lyxose, ribulose and xylose, and variants and derivatives thereof. The D-forms are most preferred. Preferably, the saccharide unit is selected from ribose and xylose, and variants and derivatives thereof. A preferred variant of ribose is deoxyribose.

A saccharide unit derived from a six carbon carbohydrate may be independently selected from allose, altrose, glucose, mannose, gulose, idose, galactose, talose and fructose, and variants and derivatives thereof. The D-forms of these carbohydrates as well as L-galactose are most preferred. Preferably the saccharide unit is selected from glucose, mannose, galactose and fructose, and variants and derivatives thereof. A preferred variant of mannose is rhamnose. A preferred variant of glucose is glucosamine. The variants daunosamine and N-acetyl-galactosamine may also be selected as a saccharide unit.

A saccharide unit may be in cyclic or acyclic form. The cyclic form of the saccharide unit is most preferred.

A sugar may be selected from monosaccharides, disaccharides, and trisaccharides, but a monosaccharide is preferred.

A saccharide unit may be a simple unmodified carbohydrate, or it may be a derivative or a variant of a carbohydrate.

A variant of a carbohydrate is a carbohydrate where one or more hydroxyl groups of a carbohydrate group is formally replaced with another group. The formal replacement group may be independently selected from an amino group, a carboxylic acid, an alkyl group, an aryl group such as a nucleobase, a sulfate group, a thiol group and a phosphate group, amongst others. A variant also includes deoxysugars, where a hydroxyl group is formally replaced with hydrogen, as for example in deoxyribose.

In one embodiment, the anomeric hydroxyl group may be replaced with another group.

Many sugars comprising variant carbohydrate groups are commercially available. Others may be readily prepared using techniques familiar to one of skill in the art.

A derivative of a carbohydrate is a carbohydrate where one or more hydroxyl groups of a carbohydrate group has been reacted to introduce something additional, for example by esterification. Derivatives also include those groups where the hydroxyl groups are protected as acetals, esters and ethers. Many carbohydrate protecting groups are known in the art. Reference may be made to Green and Wuts, Protective Groups in Organic Synthesis (3rd Edition, 1999) which is incorporated herein in its entirety, for examples.

Where a variant has a replacement group or a derivative has a substituent group, that group may provide a linker group or form part of a linker group attaching to a redox system or the conductive support.

Many sugars comprising variant carbohydrate units are commercially available. Others may be readily prepared using techniques familiar to one of skill in the art.

Additionally or alternatively, a saccharide unit may be a derivative of a variant of a carbohydrate group. For example, a hydroxyl group of a glucosamine saccharide unit may be substituted with a substituent.

One preferred monosaccharide sugar variant is glucosamine. Other glucosamine-based saccharides for use in the present invention include N-acetylglucosamine, 2-amino-2-deoxy-D-glucopyranose ($GlcNH_2$), 2-amino-2-deoxy-D-galactopyranose ($GalNH_2$) and 2-amino-2-deoxy-D-mannopyranose In other embodiments, the monosaccharide may be an N-glycoside. In certain embodiments the monosaccharide may be an N-glycoside of an amino monosaccharide, such as glucosamine, galactosamine, or mannosamine. The glycoside preferably comprises one or more amino groups. In one embodiment, the glycoside is derived from an alkyl amine, such as diethylenetriamine and ethylenediamine.

S- and O-glycoside monosaccharides may also find use in the present invention.

Oxidised and reduced monosaccharides may find use in the present invention, notably gluconic acid and glucaric acid.

In one preferred embodiment a sugar, notably ribose or deoxyribose is attached to a nucleobase. A nucleobase may be attached at the 1- or 5-position of the ribose or deoxyribose sugar and may be considered as forming part of a linker group. Together, the ribose or the deoxyribose and the nucleobase may form a nucleoside. The nucleoside may be adenosine, guanosine, 5-methyluradine, urasine, or cytidine.

A nucleobase will generally be connected to a sugar through an N-glycosidic bond. The nucleobase may be connected to a conductive support, a redox system, or a further part of a linker group through a nitrogen atom on the nucleobase.

In other embodiments, the sugar is a polysaccharide. The polysaccharide may have 50 or more, 100 or more, 500 or more, or 1,000 or more saccharide units.

Chelate Formation

Formation of a complex between a sugar and an analyte species which is ionic, for instance a metal ion or a boron ion, will generally take place by chelate formation in which the sugar acts as a ligand binding to the analyte ion. A chelate may be generated by the chelation of one or more hydroxyl groups of the sugar with the analyte species. Preferably a saccharide unit for use in binding an analyte species comprises two or three hydroxyl groups, each of which is a chelating group in the complex One or more hydroxyl groups involved in the chelation of the analyte may be deprotonated in order to form the chelate. Chelate formation may involve one saccharide unit chelating one analyte ion, but could involve different stoichiometry such as one saccharide unit chelating two ions or one ion forming chelates with two saccharide units, possibly from two different molecules.

Other functional groups may be involved in complex formation, such as carboxylic acid groups and amine groups. If these are involved, the number of hydroxyl groups involved in chelate formation may be less. Chelate-forming groups may also be located on a linker group attached to the sugar. Chelate formation between a saccharide and an ion may involve two or even three hydroxy groups or other functional groups on a single saccharide unit. Where a sugar derivative comprises a substituent group, this substituent group may be involved in chelate formation.

The steric arrangement of the hydroxyl groups on the saccharide unit may be selected to maximise analyte binding affinity. The arrangement of the hydroxyl groups may also be selected to maximise binding selectivity. Such considerations are important as it may allow the electrochemical sensor to be used to detect the presence of an analyte of interest despite the presence of other species in a fluid.

For a pyranose saccharide ring, two or three hydroxyl groups may be arranged with respect to one another in an arrangement selected from: 1,3,5-ax-ax-ax triol, 1,2,3-ax-eq-ax triol, cis-diol and trans-diol. In one embodiment the sugar comprises one or more pyranose saccharide units having at least three hydroxy groups in a 1,3,5-ax-ax-ax triol or 1,2,3-ax-eq-ax triol arrangement.

For a furanose saccharide ring, two hydroxyl groups may be arranged with respect to one another in an arrangement selected from cis-cis triol and cis-diol. In one embodiment the sugar comprises one or more furanose saccharide units having three hydroxy groups in a cis-cis triol arrangement.

The hydroxyl groups in the arrangements described above may be substituted as described for the saccharide derivatives for use in the invention, or replaced with a replacement group, as described above for the variants for use in the invention. The preferred replacement groups are amino groups and carboxylic acid groups.

The complex of the invention, as well as including chelates, also includes supramolecular complexes. Such complexes are preferred where the analyte species is not or does not contain a metal atom or a boron atom. A supramolecular complex may have hydrogen-binding interactions, π-stacking interactions and other such bonding interactions between the sugar and the analyte species.

Moieties other than sugars may also be used for binding to an analyte species. Suitable chemical structures will provide functional groups able to bind to an analytic species, notably functional groups able to chelate with metal ions. It is desirable that any binding moiety should not require elaborate synthetic chemistry.

Suitable chemical compounds may contain a plurality of hydroxyl groups (i.e. diols and polyols) able to participate in chelating of ions which are the anlyte species. One possibility is aromatic compounds with hydroxyl groups on adjacent carbon atoms of an aromatic ring, as in 2,3-dihydroxy aniline and pyrogallol i.e. 1,2,3-trihydroxy benzene.

It may be desirable that the analyte is eventually released from the immobilised compound to which it has been bound. For instance to remove analyte from a sensor positioned downhole, in order to rejuvenate that sensor for further use. This may be accomplished electrochemically. The applicant's copending application describes sugar-based material for use in the delivery of a species from a complex into a reservoir or process fluid. In the context of the present invention, the application of a voltage to the conductive support may result in alteration of the electronic configuration of the sugar or other compound to which the analyte is bound, and this change in electronic configuration may cause the bound analyte to be released from the sugar.

Linker Group

A sugar may be bound to a redox system or to a conductive solid support through a linker group. A linker group may be attached to any atom or group on the sugar. Specifically the linker may be attached to the anomeric carbon atom on the sugar. This may be referred to as a glycoside bond. Alternatively, the linker may be attached to a hydroxyl group on the sugar.

A linker group may be any group that forms a structural link to a sugar, but it is envisaged that a linker group will usually not itself contain a sugar.

In one embodiment, the linker group is derived from a nucleobase. The nucleobase together with the sugar may form a nucleoside. The nucleobase may be a natural nucleobase selected from adenine, guanine, thymine, cytosine and uracil. The nucleobase may be a modified nucleobase selected from hypoxyxanthine, xanthine and 7-methylguanosine.

In certain embodiments, a non-sugar linker group may participate with the sugar to form a complex with the component. The linker group, therefore, may function as a ligand in the complex.

Additives

In some embodiments, the electrochemical sensor may be used in combination with an additive. Such additives, may work together with the immobilised compound to bind the analyte. Notably an additive may stabilise or promote the formation of a complex between the immobilised compound and the analyte.

The additive may be added to a reservoir or process fluid by a well operator, or the additive may be a compound that is present in the reservoir or process fluid.

The additive may have an amine group and/or a hydroxyl group.

Additives having an amine group include alkylamines, such as ethylenediamine. Preferably, the additive is selected from 1,3-diaminopropane (DAP), ethylenediamine (EN), and diethylenetriamine.

Other additives include compounds having amine and hydroxyl groups.

Examples include N,N-bis[(2-pyridylmethyl)-1,3-diaminopropan-2-ol] and 2-[(pyridin-2-yl)methylamino]ethanol.

In some embodiments, an additive may be a sugar in solution. The sugar may be a sugar as described herein.

In other embodiments, the complex formed between a sugar and an analyte species does not include an additive and is formed solely from the analyte species and the immobilised analyte-binding compound.

Redox System

Preferred forms of the binding compound of this invention include a chemical moiety which provides a redox system which is separate from the moiety which binds to the analyte species but whose electrochemical properties alter when the binding moiety is attached to the analyte species. This alteration in electrochemical properties will generally arise because the binding of the analyte species will alter the chemical environment of the redox system. It is very desirable that the alteration in electrochemical properties should be observable when the redox system is exposed to pH likely to be encountered in use of the sensor of this invention. Thus it may be desirable that the altered behaviour is observable when the redox system is exposed to any value of pH in a range from pH 4 to pH 10.

A preferred redox system is a metallocene (which may be a substituted metallocene). In particular ferrocene can be used. The redox reaction of ferrocene can be written simply as:

$$Fc \rightarrow Fc^{+\bullet} + e^-$$

and can be observed by voltammetry. The oxidation and reduction peaks can be readily observed in resulting voltammogram and the peak currents occur at voltages which are effectively independent of the pH of the surrounding solution.

If a sugar in proximity to ferrocene complexes with a heavy-metal ion, the presence of this ion in the vicinity of ferrocene brings about a change in the voltages at which the peak oxidation and reduction currents are observed. The ferrocene can thus act as a "label" for binding of analyte species. Other redox systems whose reactions are independent of pH and therefore convenient for use in this invention are metallocenes of metals other than iron and tetrasubstituted phenylene diamines.

A redox system which is pH dependant could be used provided it shows oxidation and reduction under useful conditions of pH. For example the redox reaction of anthraquinone occurs at voltages which alter with pH but are observable when pH lies anywhere in a range of pH 2 two pH 10 and possibly somewhat beyond these limits. Further possible redox systems are other quinones, phthalocyanines and hydroxyl benzenes.

Immobilising on Conductive Substrate

A conductive substrate on which the binding, compound is immobilised should not be chemically degraded by exposure to the fluid to which it is exposed. Noble metals including gold, silver, platinum and palladium have traditionally been used for electrodes, and may possibly be used in this invention, especially if the sensor is to be used in a context where hydrogen sulfide is absent. Chemical attachment to noble metal is possible: for instance a ferrocene group may be functionalised with a thiol-containing group which may then be used to attach to a gold electrode support.

However, in some embodiments of this invention the substrate is provided by elemental carbon, which is not susceptible to attack by sulfides or thiol groups. The most common forms of conducting carbon used in electrode manufacture are glassy carbon, carbon fibres, carbon black, various forms of graphite, carbon paste, boron-doped diamond and carbon epoxy. One further form of carbon, which has seen a large expansion in its use in the field of electrochemistry since its discovery in 1991 is the carbon nanotube (CNT). The structure of CNTs approximates to rolled-up sheets of graphite and can be formed as either single or multi-walled tubes. Single-walled carbon nanotubes (SWCNTs) constitute a single, hollow graphite tube. Multi-walled carbon nanotubes (MWCNTs) on the other hand consist of several concentric tubes fitted one inside the other.

The immobilised compound which provides affinity for an analyte and also a redox system may itself be chemically bound to the substrate. Chemical reactions capable of binding a molecule to a substrate are known. The derivatisation procedures available for attaching to a carbon substrate encompass two main strategies of reaction. The most common involves electrochemical induced derivatisation leading to the formation of a covalent bond between a carbon electrode and the functional group. Examples (with an indication of the relevant papers in the list of references) include:

electro-oxidation of alcohols—Gou et al;

electro-oxidation of primary and secondary amines—Barbier et al and Antoniadou et al;

electro-oxidation of carboxylates—Andrieux et al;

electro-oxidation of hydrazides—Hayes and Kuhr; and electro-reduction of diazonium salts—Allongue et al.

A second and more general strategy for binding to a carbon substrate involves a homogeneous derivatisation procedure. This has focused on the oxidation of the carbon surface by a homogeneous oxidising agent such as potassium permanganate or nitric acid, which has an analogous effect to direct electrochemical oxidation by providing oxygenated functional groups on the carbon surface, which can then be chemically reacted with various moieties to functionalise the carbon. Another approach is the homogeneous reduction of diazonium compounds in reducing media—see Pandurangappa et al. WO2005/066618 describes the diazocoupling of anthraquinonyl and nitrophenyl groups onto carbon nanotubes by means of the reduction of diazonium salts.

A further possibility is that the compound may be immobilised onto the substrate by deposition from a solution in a volatile solvent which is allowed to evaporate, or by a mechanical action, such as rubbing it onto a surface of the substrate.

Some preferred compounds in which the sugar is ribose and the redox system is ferrocene are compounds of formula (I), formula (II) or formula (III), and derivatives and variants thereof:

(I)

-continued

Preferably, the sensor of the invention comprises a sugar-based assembly having a sugar and a linker group derived from a compound of formula (I), formula (II) or formula (III).

In any of these compounds, ribose may be replaced with deoxyribose.

The Analyte Species and the Role of the Sensor

The analyte species may be harmful or potentially harmful. The term "harmful" as used herein refers not only to the ability of a species to cause damage to a living organism, but also the ability of that species to cause damage to apparatus exposed to the test fluid, as well as other downstream apparatus. In one example, the analyte species may cause or catalyse the corrosion of metal piping and the like.

Additionally or alternatively, the analyte species may be a species that is capable of unwanted reaction with the reagents that will be used to treat the test fluid. The reaction of the analyte species with these reagents may result in the formation of by-products that are themselves harmful or lower the efficiency of the processing step in question, as more reagent is needed to bring about the desired transformation of the test fluid.

The present invention provides a sensor that allows harmful or otherwise undesirable species to be detected in a fluid. Where these species are detected in a fluid, appropriate action may be taken by the operator to remove the species concerned or otherwise minimise the harmful effect. Additionally or alternatively; the analyte species may be a high value commodity which the operator will wish to recover if it is found to be present in sufficient quantity.

The analyte is preferably an ion, notably a metal cation or a non-metal anion. The ion may be a naked ion, that is an ion which is not associated with any ligands other than solvent ligands. Alternatively, the analyte ion may be encountered in a form where it is associated with one or more ligands. The sugar (or other immobilised compound) may competitively displace one or more of these ligands ("substitution") to form a complex as described herein. Alternatively the sugar-based assembly may form a complex with the ion without displacement of a ligand ("addition"). Additionally, the ion may also be bound by any linker group. The overall charge of the complex which is formed may be different to the charge on the ion before chelation. Thus, a neutral complex may be formed even though the analyte ion within the complex is itself charged.

The oxidation state of an ion within a reservoir or process fluid may change as the fluid moves through the reservoir, through the well bore and to the surface. The change in oxidation state may be as a result of the ion coming into contact with a more oxidising environment. For instance, the fluid may become exposed to air.

A specific example concerns Cr (III) within a reservoir or process fluid. This may become oxidised to Cr (VI) under certain recovery conditions. The latter ion is particularly toxic, and is believed to be carcinogenic. Detection and removal of this ion from a reservoir or process fluid is particularly desirable. Alternatively, the Cr (III) ion may be recovered from the fluid instead, prior to its conversion to its toxic relation.

The electrochemical sensor of the present invention may be used to detect the presence of an analyte species in a fluid before that analyte is able to react. The reservoir and process fluid may then be treated to remove the analyte species, thereby minimising the formation of the reaction product, which may be harmful. The sensor may also be used to monitor the change in oxidation state of the analyte species. In more general aspects, the sensor may be used to detect any chemical change in an analyte species, or a change in the physical state of a fluid as it passes through a reservoir or other flow path.

The sensor of the invention may be used to detect two or more analyte species within a family of similar compounds or ions. For example, the analytes may be ions of the same element in different oxidation states. Alternatively, the analyte species may be ions of different elements of the same oxidation state within the same group. Hence, the sensor may be used to detect the presence of analyte species within a family, where those analyte species may have similar properties, for example similar reactivities.

The non-metal ion may be a boron ion, notably anionic boron, or may be a metal ion independently selected from the ions of a Group 2, Group 5, Group 6, Group 8, Group 9, Group 10, Group 11, or Group 12 metal and may be the ion of a heavy metal.

More specifically an ion may be independently selected from the ions of the non-metal B and the metals Ca, Cu, Fe, Co, Ni, Ba, Ca, Sr, Mo, W, Zn, Cd, Hg, Mg, Ra, Pb, Pd, Pt, and V.

A metal ion may be independently selected from Ca (II), Cu (II), Fe (III), Co (II), Co (III), Co (IV), Ni (II), Ba (II), Ca (II), Sr (II), Mo (VI), W (VI), Zn Cd (II), Hg (II), Pb (II) and V.

The sensor of the invention may in particular be used to detect analyte ions that are associated with scale formation or wastewater contamination and toxic ions such as lead and mercury.

A scaling ion may be an ion that is present in a scale selected from calcium carbonate (calcite), magnesium silicate, amorphous silica, calcium sulfate dihydrate (gypsum), strontium sulfate (celestite), and iron sulfide and iron carbonate. The scaling ion may be selected from Ca, Mg, Ba, Sr, Ra, and Fe.

A waste water ion contaminant may be an ion that is present in water at a concentration above the maximum that is permitted for the safe or legal disposal of the water into the environment, for example, into the sewer or for release into storage ponds. The sensor of the invention may be used to detect the presence of the ion, and action may be taken, if appropriate, to reduce the concentration of that ion to a level at which it is permitted to release the water into the environment.

The waste water ion contaminant may be selected from As, Ba, Cd, Cr, Cu, Fe, Pb, Mn, Hg, Mo, Ni, Se, Hg, Sn, or Zn.

Hg and its ions such as Hg(II) are recognised as having the potential to seriously damage the surfaces of reservoir fluid processing facilities. Particularly, Hg is known to damage Al-based heat exchangers. Pb and its ions are recognised as being harmful to the environment and are particularly, undesirable as contaminants of an aquifer fluid.

Test Fluids

The electrochemical sensors of the present invention are particularly suitable for use in the detection of analyte species in reservoir fluids in an oilfield, and the process fluids that are used to gain access to and promote recovery of those reservoir fluids. The sensors may also find use in the detection of analyte species in subterranean waterbodies such as aquifers which may or may not be associated with an oilfield.

A sensor may be used to quantify the amount of an analyte species in the fluid, and also to detect changes in the amount of that analyte over time.

The fluid that is brought into contact with an electrochemical sensor may not contain the analyte of interest. The fluid may be free of that analyte, and the electrochemical sensor may be used to determine that this is indeed the case. The fluid may then be processed as appropriate, as the operator is reassured that the particular analyte is not present in the fluid.

The reservoir or process fluid that is contacted with the electrochemical sensor may be a sample taken from the main body of that fluid. Alternatively the electrochemical sensor may be such that it is available to contact the main body of fluid without the need for separation of a sample.

In a general aspect, the present invention provides an electrochemical sensor for use in the detection of an analyte species from any fluid that is located at a subterranean location or is taken from a subterranean location. It is preferred that the subterranean location is a reservoir. The subterranean location may also be a wellbore.

A reservoir fluid, (which may be a fluid that is located in or is taken from a subterranean reservoir at least 100 m, often at least 1,000 m below the surface) may be formation water or connate water from a hydrocarbon reservoir, or may be water from a subterranean aquifer.

Alternatively the reservoir fluid may be a fluid that is introduced into a subterranean location during any one or more of the oilfield or aquifer exploration, appraisal, production, development and close phases. The reservoir fluid may be a drilling fluid or a well treatment fluid.

Significant forms of this invention relate to the use of a sensor with reservoir or process fluids at a subterranean location. In other embodiments of the invention, the reservoir or process fluid may be analysed at a surface location. A sensor of this invention may also be used to analyse wastewater that is not taken from a subterranean reservoir. Wastewater may be effluent from an industrial process performed at the surface. It may also include aqueous effluent from residential properties, e.g. sewerage. Wastewater may also be referred to as surface water.

EXAMPLES

These examples show synthetic routes to compounds containing a ribose sugar or other moiety with hydroxyl groups available for chelate formation and also containing ferrocene as a redox system. The compound will then be immobilised on a conductive support as mentioned above. A possibility is that the ferrocene group may be derivatised for chemical attachment to an electrode support.

In the case of a ribose-based compound a linker group containing ferrocene may be attached at the 1-position or 5-position of the ribose sugar. The linker may comprise a nucleobase, in which case the ribose sugar and the nucleobase together may form a nucleoside. In some of these examples the nucleobase is adenine which adenine forms a C—N glycosidic bond to the ribose sugar. The sugar and the linker therefore form an adenosine nucleoside.

Reaction Between Dimethylaminomethyl Ferrocene and D-Ribofuranose.

Dimethylaminomethyl ferrocene can react with methyl iodide to form the corresponding quaternary ammonium salt, as shown below. (Ferrocenylmethyl)trimethylammmonium iodide has been extensively used as a staffing material for the synthesis of different ferrocenylmethyl-compounds (see Bidstein et al. and Xiao et al.).

(Ferrocenylmethyl)trimethylammonium iodide may be reacted with a derivatised D-ribofuranose molecule. This may be achieved by firstly protecting the 2,3-dihydroxy group, and then treatment with NaH in DMF at low temperature to form the corresponding sodium alcoholate. This is an excellent nucleophile to proceed with the nucleophilic substitution of (ferrocenylmethyl)trimethylammonium iodide.

Finally, the protecting groups for the 2,3-dihydroxyl groups are deprotected.

R may be a derivative group as described above. The ferrocene moiety may be attached to an electrode support either directly or via a further linker section.

Reaction Between Ferrocenecarboxaldehyde and Adenosine.

Ribose-based assemblies having a linker comprising a ferrocene group and a nucleobase may be prepared by the reductive alkylation of adenosine with ferrocenecarboxaldehyde (also called formylferrocene) and Pd-phthalocyanine by (60-89% yield) (see Eckert et al. 1986 and 1991).

The ferrocene moiety may be attached to an electrode support either directly or via a further linker section.

Reaction Between Ferrocenecarboxaldehyde and 3,4 Dihydroxy Aniline 3,4-(Methylenedioxy)aniline (available from Sigma-Aldrich) can be cleaved to 3,4-dihydroxyaniline (also named as 1,2 dihydroxy 4-aminobenzene) by treatment with $AlBr_3$, EtSH, 0° C., 0.5-1 h, in accordance with the procedure of Node et al.

Once this 4-amine-1,2-benzenediol is prepared, the amine group can react with ferrocenylcarboxaldehyde in a similar way to that described above for adenosine:

The two hydroxyl groups on adjacent carbon atoms of the benzene ring are available for chelation with a metal ion.

Reaction Between Dimethylaminomethyl Ferrocene and Pyrogallol

Partially protected pyrogallol may be reacted with (ferrocenylmethyl)trimethylammonium iodide as shown below:

R1 and R2 may both be any convenient alkyl group such as methyl or ethyl. Subsequent deprotection will give 1,2 dihydroxy-3(ferrocenylmethoxy)benzene:

-continued

Here again, the two hydroxyl groups on adjacent carbon atoms of the benzene ring are available for chelation with a metal ion.

REFERENCES

The following references are incorporated by reference herein in their entirety.
GB 2 391 314
GB 2 409 902
GB 2 430 749
GB 2 420 849
GB 2 395 555
GB 2 404 252
US 2001/0042693
U.S. Pat. No. 5,296,123
U.S. Pat. No. 5,437,772
U.S. Pat. No. 5,676,820
WO 2005/066618
Yu E Alexeev, I S Vasilchenko, B I Kharisov, L M Blanco, A D Garnovskii and Yu A Zhdanov, Journal of Coordination Chemistry, 57 (2004) 1447-1517;
P Allongue, M Delamer, B Desbat, O Fagebaume, R Hitmi, J Pinson and J M Saveant, J. Am. Chem. Soc., 119, (1997) 201.
C P Andrieux, F Gonzalez and J M Saveant, J. Am. Chem. Soc., 119, (1997) 4292;
S Antoniadou, A D Jannaloudis, P D Jannadoukakis and E Theodoriu, J. Appl. Electrochem., 22, (1992) 1060;
B Barbier, J Pinson, G Desarmot and M Sanchez, J. Electrochem. Soc., 137 (1990) 135;
P D Beer, Acc Chem Res 31 (1998) 71-80;
B Bidstein, M Malaun, H Kopacka, K.-H Ongania and K Wurst, J. Organometallic Chem., 552 (1998) 45;
H Eckert and C Seidel, Angew. Chem. Int. Ed. Engl., 25 (1986) 159;
H Eckert, B Forster and C Seidel Zeitschrift für Naturforschung B, A journal of chemical sciences 49 (1991) 339;
B. Gou, J. Anzai and T. Osa, Chem. Pharm. Bull., 44 (1996) 860;
M A Hayes and W G Kuhr, Anal. Chem., 71 (1999) 1720;
B A Keay and R Rodrigo, J. Am. Chem. Soc., 104, (1982) 4725;
A S Kende and D P Curran, J. Am. Chem. Soc., 101 (1979) 1857;
J C Medina, T T Goodnow, M T Rojas, J L Atwood, B C Lynn, A E Kaifer and G W Gokel, J. Am. Chem. Soc., 114 (1992) 10583-10595;
M Node, K Nishide, M Sai, K Ichikawa, K Fuji, E Fujita, Chem. Lett., 1979 page 97;
M Pandurangappa, N S Lawrence and R G Compton, Analyst, 127 (2002) 1568;
H Plenio and C Aberle, Chemical Communications 24 (1998) 2697-2698;
H Plenio and C Aberle, Organometallics 16 (1997) 5950-5957;
H Plenio and D Burth, Organometallics 15 (1996) 4054-4062;
L Xiao, R Kitzler, and W Weissensteiner, J. Org. Chem., 66 (2001) 8912-8919;
F W Ziegler, K W Fowler and S Kanfer, J. Am. Chem. Soc., 98 (1976) 8282;
A Zirino, S H. Lieberman, and C Clavell, Environ. Sci. Technol. 12 (1978) 73.

The invention claimed is:

1. A method of detecting an analyte species in a liquid, the analyte species being selected from ions of the non-metal B and ions of the metals Cu, Fe, Co, Ni, Ba, Ca, Sr, Mo, W, Zn, Cd, Hg, Mg, Ra, Pb, Pd, Pt, and V, the method comprising:
providing an electrochemical sensor comprising:
a solid electrically conductive substrate and
at least one compound immobilized thereon which contains both a sugar which is a di- or poly-hydroxy compound with binding affinity for the analyte species to be detected and a non-sugar redox system which displays electrochemical oxidation/reduction behaviour which is modified when the sugar binds the analyte species to be detected,
wherein the sugar and the non-sugar redox system are connected directly or indirectly through one or more covalent bonds
contacting the liquid with the sensor, for binding of the analyte to the said compound immobilized on the substrate, and measuring the electrochemical oxidation/reduction behaviour of the redox system of said compound immobilized on the substrate.

2. A method according to claim 1 wherein measurement of the electrochemical oxidation/reduction behaviour of the redox system of the said immobilised compound is carried out by voltammetry.

3. A method according to claim 1 wherein the ionic analyte species is selected from ions of the metals Ca, Mg, Ba, Sr, Ra and Fe.

4. A method according to claim 1 wherein the sugar has a five or six membered carbohydrate ring.

5. A method according to claim 1 wherein the sugar has a five or six membered carbohydrate ring with modifications to one, two or three of the hydroxyl groups of the carbohydrate ring.

6. A method according to claim 1 wherein the liquid is a subterranean water body and the sensor is incorporated in a tool suspended in a well communicating with the subterranean water body.

7. A method according to claim 1 wherein the liquid is in a wellbore and the sensor is in a tool suspended in the wellbore.

8. A method according to claim 1 wherein the tool is a wireline tool or a slickline tool.

9. A method according to claim 1 wherein the redox system undergoes electrochemical oxidation and reduction reactions in aqueous solution, and properties of the reactions are altered when the sugar binds the analyte.

10. A method according to claim 9 wherein voltages at which maximum redox reaction occurs are altered when the first moiety binds the analyte and measurement of the electrochemical oxidation/reduction behaviour of the redox system of the said immobilised compound is carried out by voltammetry.

11. A method of detecting an ionic analyte species in a liquid, the analyte species being selected from ions of the non-metal B and ions of the metals Ca, Cu, Fe, Co, Ni, Ba, Ca, Sr, Mo, W, Zn, Cd, Hg, Mg, Ra, Pb, Pd, Pt, and V, the method comprising:

providing an electrochemical sensor comprising:
- a solid electrically conductive substrate and
- at least one compound immobilized thereon which has binding affinity for an ionic analyte species to be detected and displays electrochemical oxidation/reduction behaviour which is modified upon binding of the analyte,
    - wherein the compound contains both a first moiety with binding affinity for the analyte and a second moiety which is a redox system connected to the first moiety through one or more covalent bonds and whose electrochemical oxidation/reduction properties become modified when the first moiety binds the analyte, contacting the liquid with the sensor, for binding of the analyte to the said compound immobilized on the substrate, and measuring the electrochemical oxidation/reduction behaviour of the redox system of the said compound immobilized on the substrate.

12. A method according to claim 11 wherein measurement of the electrochemical oxidation/reduction behaviour of the redox system of the said immobilised compound is carried out by voltammetry.

13. A method according to claim 11 wherein the ionic analyte species is selected from ions of the metals Ca, Mg, Ba, Sr, Ra and Fe.

14. A method according to claim 11 wherein the conductive substrate is carbon-based.

15. A method according to claim 11 wherein the redox system displays electrochemical oxidation and reduction when in contact with aqueous solution having pH in the range from pH 4 to pH 10.

16. A method according to claim 11 wherein the redox system is a metallocene.

17. A method according to claim 11 wherein the liquid is a subterranean water body and the sensor is incorporated in a tool suspended in a well communicating with the subterranean water body.

18. A method according to claim 11 wherein the redox system undergoes electrochemical oxidation and reduction reactions in aqueous solution, and properties of the reactions are altered when the first moiety binds the analyte.

19. A method according to claim 18 wherein voltages at which maximum redox reaction occurs are altered when the first moiety binds the analyte and measurement of the electrochemical oxidation/reduction behaviour of the redox system of the said immobilised compound is carried out by voltammetry.

20. A method according to claim 11 wherein the liquid is in a wellbore and the sensor is in a tool suspended in the wellbore.

21. A method according to claim 20 wherein the tool is a wireline tool or a slickline tool.

* * * * *